(12) United States Patent
Wang et al.

(10) Patent No.: US 11,690,580 B2
(45) Date of Patent: Jul. 4, 2023

(54) SUPPORTING DEVICE IN MEDICAL DIAGNOSTICS SYSTEM

(71) Applicant: SHANGHAI UNITED IMAGING HEALTHCARE CO., LTD., Shanghai (CN)

(72) Inventors: Yun Wang, Shanghai (CN); Huang Yan, Shanghai (CN); Wei Qi, Shanghai (CN); Jian Liu, Shanghai (CN); Jiamin Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 103 days.

(21) Appl. No.: 17/239,608

(22) Filed: Apr. 25, 2021

(65) Prior Publication Data
US 2021/0244369 A1    Aug. 12, 2021

Related U.S. Application Data

(62) Division of application No. 15/317,366, filed as application No. PCT/CN2016/074654 on Feb. 26, 2016, now Pat. No. 10,987,070.

(30) Foreign Application Priority Data

Aug. 7, 2015    (CN) .......................... 201520594134.0
Sep. 11, 2015   (CN) .......................... 201510578351.5

(51) Int. Cl.
*A61B 6/04*    (2006.01)
*A61G 13/12*   (2006.01)
(Continued)

(52) U.S. Cl.
CPC ............ *A61B 6/0407* (2013.01); *A61B 5/704* (2013.01); *A61B 6/032* (2013.01); *A61B 6/0421* (2013.01);
(Continued)

(58) Field of Classification Search
CPC ....... A61B 5/704; A61B 6/032; A61B 6/0407; A61B 6/0421; A61B 6/0487;
(Continued)

(56) References Cited

U.S. PATENT DOCUMENTS 5,013,018 A    5/1991   Sicek et al.
5,960,054 A    9/1999   Freeman et al.
(Continued)

FOREIGN PATENT DOCUMENTS

CN    1161190 A    10/1997
CN    1759807 A    4/2006
(Continued)

OTHER PUBLICATIONS

International Search Report in PCT/CN2016/074654 dated May 23, 2016, 5 pages.
(Continued)

*Primary Examiner* — David R Hare
*Assistant Examiner* — Alexis Felix Lopez
(74) *Attorney, Agent, or Firm* — Metis IP LLC

(57) ABSTRACT

A device and system for supporting a patient or an object in an examination is provided. The supporting system may include a portion for supporting the body of a patient and/or a head supporting device. The portion for supporting the body may move in one or more directions. The head supporting device may be adjust to meet requirements of imaging when the patient or the object is supine or prone.

20 Claims, 9 Drawing Sheets

(51) Int. Cl.
*A61B 6/00* (2006.01)
*A61G 13/02* (2006.01)
*A61B 5/00* (2006.01)
*A61B 6/03* (2006.01)
*A61G 13/06* (2006.01)

(52) U.S. Cl.
CPC .......... *A61B 6/4417* (2013.01); *A61B 6/4441* (2013.01); *A61B 6/504* (2013.01); *A61G 13/02* (2013.01); *A61G 13/06* (2013.01); *A61G 13/121* (2013.01); *A61B 6/0487* (2020.08); *A61B 6/501* (2013.01)

(58) Field of Classification Search
CPC ..... A61B 6/4417; A61B 6/4441; A61B 6/501; A61B 6/504; A61G 13/02; A61G 13/06; A61G 13/121
See application file for complete search history.

(56) References Cited

U.S. PATENT DOCUMENTS

| | | | |
|---|---|---|---|
| 6,094,760 | A | 8/2000 | Nonaka et al. |
| 6,698,045 | B1 * | 3/2004 | Coppens ................ A61G 13/12 128/869 |
| 7,555,794 | B2 * | 7/2009 | Zelnik .................. A61B 6/0421 5/636 |
| 7,697,971 | B1 | 4/2010 | Green, Jr. et al. |
| 2001/0003218 | A1 | 6/2001 | Schaefer |
| 2002/0039403 | A1 | 4/2002 | Oota |
| 2002/0180397 | A1 | 12/2002 | Henley et al. |
| 2007/0094796 | A1 | 5/2007 | Bartels et al. |
| 2009/0028290 | A1 | 1/2009 | Grebner et al. |
| 2011/0215259 | A1 | 9/2011 | Iwata |
| 2012/0023671 | A1 | 2/2012 | Miyano et al. |
| 2017/0325754 | A1 | 11/2017 | Pettinato et al. |

FOREIGN PATENT DOCUMENTS

| | | |
|---|---|---|
| CN | 201200415 Y | 3/2009 |
| CN | 103750852 A | 4/2014 |
| CN | 105078504 A | 11/2015 |
| CN | 204971342 U | 1/2016 |
| JP | 2002291731 A * | 10/2002 |
| JP | 2009000321 A * | 1/2009 |
| JP | 4603712 B2 * | 12/2010 |
| JP | 5047705 B2 * | 10/2012 |

OTHER PUBLICATIONS

Written Opinion in PCT/CN2016/074654 dated May 23, 2016, 5 pages.
The Extended European Search Report in European Application No. 16815529.9 dated Aug. 29, 2018, 10 pages.
First Office Action in Chinese Application No. 201510578351.5 dated Jun. 2, 2017, 19 pages.
The Fifth Office Action in Chinese Application No. 201510578351.5 dated Jan. 25, 2018, 20 pages.

* cited by examiner

SUPPORTING DEVICE IN MEDICAL DIAGNOSTICS SYSTEM

CROSS-REFERENCE TO RELATED APPLICATIONS

The application is a divisional application of U.S. application Ser. No. 15/317,366, filed on Dec. 8, 2016, which is a U.S. national stage under 35 U.S.C. § 371 of International Application No. PCT/CN2016/074654, filed on Feb. 26, 2016, designating the United States of America, which claims priority to Chinese Patent Application No. 201520594134.0 filed on Aug. 7, 2015, and Chinese Patent Application No. 201510578351.5 filed on Sep. 11, 2015, the entire contents of each of which are hereby incorporated by reference.

TECHNICAL FIELD

The present disclosure relates generally to a supporting system or structure, and more specifically, to a system or structure for supporting a patient or an object used in an examination system.

BACKGROUND

Modern medical diagnostics generally relates to support an object or a patient under examination on a supporting device such as a table or a bed and to scan and diagnose the object or the patient in a corresponding apparatus. Typically, the apparatus and the supporting device are specially designed for and used in a particular medical diagnosis system. For instance, an X-ray computerized tomography (hereinafter referred to as CT) bed can only be used together with a CT scanner to perform a CT scan.

A plurality of medical examination techniques may be used either individually or concurrently in a diagnosis. A patient may need to either walk to or be moved between different examination devices to undergo different examinations. After the patient is moved from a first examination using a first examination device to a second examination using a second examination device, the patient may need to be readjusted to a desired posture before the second examination may be performed. Due to the move, the readjustment may be needed even if the desired posture in the first examination is the same or similar to the desired posture in the second examination.

In some examinations, a patient may need to maintain a specific posture for an examination to be properly performed. An examination performed when the patient fails to maintain a satisfactory body posture may introduce artifacts. Moreover, repeated adjustments of the posture of the patient and/or repeated attempts to perform the examination may increase not only time and costs, but also exposure to one or more agents used in the examination. For instance, if a radiation based imaging examination is involved, repeated attempts to perform the examination may increase the radiation exposure to the patient.

There is a need for a supporting system for supporting the person undergoing a plurality of examinations using a plurality of examination devices. There is also a need for a support device for helping a patient to maintain a desired posture in one or more examinations.

SUMMARY

The present disclosure relates generally to a multi-modality diagnostic imaging system, and more specifically to a system or structure for supporting a patient or an object lying thereon used in multi-modality diagnostic imaging system.

According to one aspect of the present disclosure, a supporting system may comprise a table for supporting a patient or an object, a stand for supporting the table, a guide device located in a first plane for supporting the stand. According to one aspect of the present disclosure, the stand may have a length direction and a width direction. According to one aspect of the present disclosure, the guide device may have a length direction. According to one aspect of the present disclosure, the stand and the table may be arranged to form a space underneath the table for placing an examining device. According to one aspect of the present disclosure, the stand may be movably connected to the guide device.

According to one aspect of the present disclosure, the length direction of the table may be parallel to the length direction of the guide device. According to one aspect of the present disclosure, the length direction of the table may perpendicular to the length direction of the guide device.

According to one aspect of the present disclosure, a projection of contact area of the table and the stand onto the first plane partially overlaps with a projection of contact area of the guide device and the stand onto the first plane.

According to one aspect of the present disclosure, the table may be fixedly attached onto the stand. According to one aspect of the present disclosure, the table may be movably attached onto the stand.

According to one aspect of the present disclosure, the table may have a first position in which a projection of the table onto the first plane does not overlap with a projection of the guide device onto the first plane. According to another aspect of the present disclosure, the table may be configured to move along the width direction of the table to the first position. According to one aspect of the present disclosure, the table may have a second position in which a projection of the table onto the first plane at least partially overlap with a projection of the guide device onto the first plane. According to a further aspect of the present disclosure, the table may be configured to move along the width direction of the table to the second position.

According to one aspect of the present disclosure, the supporting system may further comprise a first driving device configured to drive the stand to move along the length direction of the guide device. According to another aspect of the present disclosure, the first driving device may comprise a guiding element placed on the guide device for moving along the length direction of the guide device, a slider placed in a contact region of the guide device and the stand, and a motor for driving the slider moving along the guiding element.

According to one aspect of the present disclosure, the stand may be configured to drive the table to move in a vertical direction. According to another aspect of the present disclosure, the stand may be configured to drive the table to rotate.

The present disclosure also relates generally to a system or structure for head supporting used in multi-modality diagnostic imaging system. According to one aspect of the present disclosure, a head supporting device may comprise a frame for supporting a shoulder of a patient, a pad placed on the frame for supporting the head of the patient. According to another aspect of the present disclosure, the pad may comprise a first surface and a second surface, and the pad may have a first working position and a second working position. According to a further aspect of the present disclosure, in the first working position of the pad, the first surface may be configured to support the jaw of the patient when the patient is prone, and in the second working position of the pad, the second surface being configured to support the head and the neck of the patient when the patient is supine. According to a further aspect of the present disclosure, the head supporting device may be configured to position the head of the patient such that an angle between the plane perpendicular to the orbitomeatal line of the patient and the vertical direction may be between 15 degrees and 20 degrees. According to a further aspect of the present disclosure, the frame may have a groove, and the pad may be embedded in the groove.

According to one aspect of the present disclosure, the pad may comprise an undersurface opposite to the first surface, a first side connected to the undersurface and the first surface. According to a further aspect of the present disclosure, the head supporting device may further comprise a second surface including the first side and the undersurface. According to a further aspect of the present disclosure, when the patient is supine, the first side may be used for supporting the neck of the patient and the undersurface may be used for supporting the head of the patient.

According to one aspect of the present disclosure, the pad may comprise a second side connected to the first surface and the undersurface. According to another aspect of the present disclosure, the second side may be opposite to the first side. According to a further aspect of the present disclosure, when the patient is prone, the undersurface may contact bottom of the groove, and when the patient is supine, the second side may contact at least a portion of the groove.

According to one aspect of the present disclosure, a first angle between a first intersection line of a second plane and the undersurface and a second intersection line of the second plane and the second side may be between 70 degrees and 75 degrees, and the second plane may be perpendicular to a length direction of the groove. According to another aspect of the present disclosure, a second angle between a third intersection line of the second plane and the first side and the second intersection line being from 20 degrees to 60 degrees.

The present disclosure also relates generally to a multi-modality diagnostic imaging system. According to one aspect of the present disclosure, an examination system may comprise a supporting system, a first examining device and a second examining device. According to another aspect of the present disclosure, the first examining device may receive at least a portion of the table of the supporting device when the first examining device performs a first examination on the patient. According to another aspect of the present disclosure, the second examining device may occupy at least a portion of the space underneath the table of the supporting system when the second examining device performs a second examination on the patient. According to a further aspect of the present disclosure, the first examining device may comprise a CT scanner, an MM machine, or a PET/CT system. According to a yet further aspect of the present disclosure, the second examining device may be an angiographer.

According to one aspect of the disclosure, a supporting system may comprise a table for supporting a patient or an object, a stand for supporting the table, a guide device for supporting the stand, a head supporting device.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
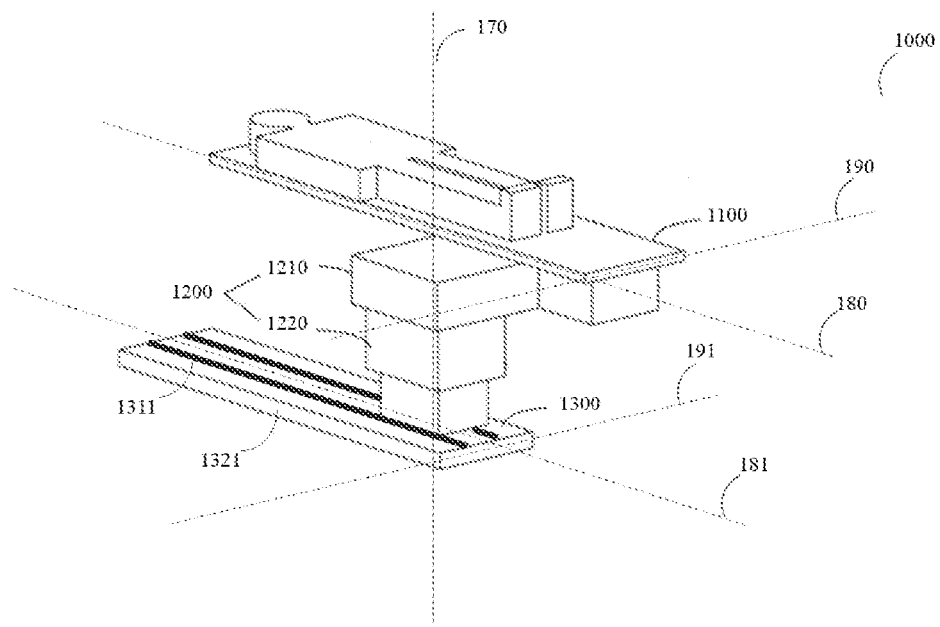
FIG. 1 and FIG. 2 show an exemplary supporting system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, devices, holders, and/or drivers have been described at a relatively high-level, without detail, in order to avoid unnecessarily obscuring aspects of the present disclosure.

It will be understood that when a device, driver or holder is referred to as being "on," "connected to," or "coupled to" another device, driver or holder, it may be directly on, connected or coupled to the other device, driver or holder, or intervening device, driver or holder may be present, unless the context clearly indicates otherwise. As used herein, the term "and/or" includes any and all combinations of one or more of the associated listed items.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. It is understood that the drawings are not to scale.

The present disclosure relates generally to a supporting system or device, and more specifically to a system or device for supporting a patient or an object used in an examination system. Some embodiments relate to a supporting system for supporting a patient or an object. The supporting system may be configured to allow the patient or the object to go through multiple examinations without changing to a different supporting system or moving the supporting system. The supporting system may include various components that may form a space for accommodating a first examination device using which the patient or the object may be subject to a first examination; the supporting system may provide support for the patient or the object for a second examination using a second examination device. Some embodiments relate to a device for supporting a portion of a patient or an object for examination under different positions. For brevity, a patient, as used herein, may include an object. As used herein, a patient may include a human patient, an animal, or a portion thereof.

FIGS. 1-12 illustrate exemplary supporting systems. A supporting system may support, position, and/or transport a patient or an object relative to an examination system. Exemplary examination systems may include a digital subtraction angiography (DSA) system, a magnetic resonance imaging (MRI) system, a magnetic resonance angiography (MRA) system, a computed tomography (CT) system, a computed tomography angiography (CTA) system, an ultrasound scanning (US) system, a positron emission tomography (PET) system, a single-photon emission computerized tomography (SPECT) system, a CT-MR system, a CT-PET system, a CT-SPECT system, a DSA-MR system, a PET-MR system, a PET-US system, a SPECT-US system, a TMS (transcranial magnetic stimulation)-MR system, a US-CT system, a US-MR system, an X-ray-CT system, an X-ray-MR system, an X-ray-portal system, an X-ray-US system, a Video-CT system, a Video-US system, or the like, or any combination thereof.

FIG. 1 shows an exemplary supporting system according to some embodiments. The supporting system 1000 may include a table 1100, a support device 1200, a guide device 1300, and a driving device (not shown in FIG. 1). The table 1100 may be configured to support, position, and/or transport a patient or an object. The table 1100 may include a plane having a length direction 180 and a width direction 190. As used herein, the length direction 180 may be the direction from the head to the feet of a patient when lying (as intended) on the table 1100 for examination. As used herein, the width direction 190 may be perpendicular to the length direction 180. The plane may be flat or essentially flat. In some embodiments, the plane may have the shape of a U-shape, a circle, a triangle, a pentagon, or the like, or a combination thereof. In some embodiments, the table 1100 may be configured to move relatively to the support device 1200 along a direction. In some embodiments, the table 1100 may be configured to move relatively to the support device 1200 along the length direction 180 of the table 1100. In some embodiments, the table 1100 may be configured to move relatively to the support device 1200 along the width direction 190 of the table 1100. In some embodiments, the table 1100 may be configured to rotate around the driving device placed between the table 1100 and the support device 1200.

The support device 1200 may be configured to support, position and/or transport the table 1100. In some embodiments, the support device 1200 may be a fixed structure with predetermined three-dimensional size. In some embodiments, the support device 1200 may be an extensible structure. For instance, the support device 1200 may extend or contract along a vertical direction 170. As used herein, the vertical direction may be the direction perpendicular to the plane of the table 1100. The table 1100 may move along the vertical direction 170 along with the extension or contraction of the support device 1200. In some embodiments, the projection of the table 1100 does not overlap with the projection of the guide device 1300; one or both of the projections may be onto the ground or the plane where the guide device 1300 is located. The table 1100 may be fixedly or slidably connected to the support device 1200.

In some embodiments, the support device 1200 may include a sliding device 1220 and a first holder 1210. The sliding device 1220 may be fixedly or slidably connected to the first holder 1210. In some embodiments, the sliding device 1220 may be slidably connected to the guide device 1300. In some embodiments, the sliding device 1220 may include a fixed structure with a predetermined height. In some embodiments, the sliding device 1220 may include an extendable structure that may extend or contract in the vertical direction 170, causing the support device 1200 to extend or contract in the vertical direction 170.

The first holder 1210 may contact, support, or be connected to the table 1100. The contact, support, or connection may include a fixed connection or a slidable connection. In some embodiments, the first holder 1210 may be connected to one end of the table 1100 along the length direction 180. In some embodiments, at least a portion of the first holder 1210 may contact, or be connected to or supported by the sliding device 1220. In some embodiments, at least a portion of the first holder 1210 may protrude outside of the sliding device 1220. For instance, as illustrated in FIG. 1, at least a portion of the first holder 1210 may extend along the width direction of the table 1100. In some embodiments, the region (or referred to as contact area) of the first holder 1210 that contacts, supports, or is connected to the table 1100 may partially overlap with the region (or referred to as contact area) of the first holder 1210 that contacts, or is supported by or connected to the sliding device 1220. In some embodiments, the region (or referred to as contact area) of the first holder 1210 that contacts, supports, or is connected to the table 1100 does not overlap with the region (or referred to as contact area) of the first holder 1210 that contacts, or is supported by or connected to the sliding device 1220. In some embodiments, the table 1100 may be slidably connected to the first holder 1210 such that the table 1100 may move along the width direction 190 on the first holder 1210. In some embodiments, the table 1100 may be fixedly connected to the first holder 1210, and the first holder 1210 may extend along the width direction 190 of the table 1100, causing the table 1100 to move along the width direction 1100. In some embodiments, the first holder 1210 may be configured to rotate around the driving device placed between the first holder 1210 and the sliding device 1220, causing the table 1100 to rotate.

The guide device 1300 may be configured to support, position and/or transport the support device 1200. In some embodiments, the guide device 1300 may be one or more (e.g., a pair of) guide rails 1311. In some embodiments, the guide rail(s) 1311 may be placed on the ground (or referred to as floor as used herein) where the support device 1200 is supported. In some embodiments, the guide device 1300 may include a base 1321 and one or more (e.g., a pair of) guide rails 1311. The guide rail(s) 1311 may be placed on or located within the surface of the base 1321. In some embodiments, the support device 1200 may be configured to move relatively to the guide device 1300. The region that the guide device 1300 occupies may be defined by the region that the guide rail(s) occupies/occupy. Merely by way of example, if the guide device 1300 includes one guide rail 1311 (located on the ground or the base 1321), the region of the guide device 1300 may include the region that the guide rail occupies. As another example, if the guide device 1300 includes a pair of guide rails 1311 (located on the ground or the base 1321), the region of the guide device 1300 may include the region defined by the two guide rails 1311, including the sub-region located between the pair of guide rails 1311. The projection of the guide device 1300 may refer to the projection of the region that the guide device 1300 occupies onto the ground or the plane where the guide device 1300 is located.

In some embodiments, the support device 1200 may be configured to move relatively to the guide device 1300 along a length direction 181 of the guide device 1300. As used herein, the length direction 181 of the guide device may refer to the direction along which the support device 1200 may move on the guide device 1300. If the support device 1200 may move on the guide device 1300 along two or more directions, the length direction 181 of the guide device may refer to the direction along which the support device 1200 may move a longer distance than along the other one or more directions. In some embodiments, the support device 1200 may be configured to move relatively to the guide device 1300 along the width direction 191 of the guide device 1300. As used herein, the width direction 191 of the guide device 1300 may be perpendicular to the length direction 181 of the guide device 1300.

In some embodiment, the guide device 1300 may be essentially straight. It should be appreciated by those skilled in the art that shape of the guide device 1300 disclosed herein is not limited to such a shape. Exemplary configurations of the guide device 1300 according to other embodiments may include essentially C-shape, essentially U-shape, essentially S-shape, or the like, or a combination thereof.

Figure 2:
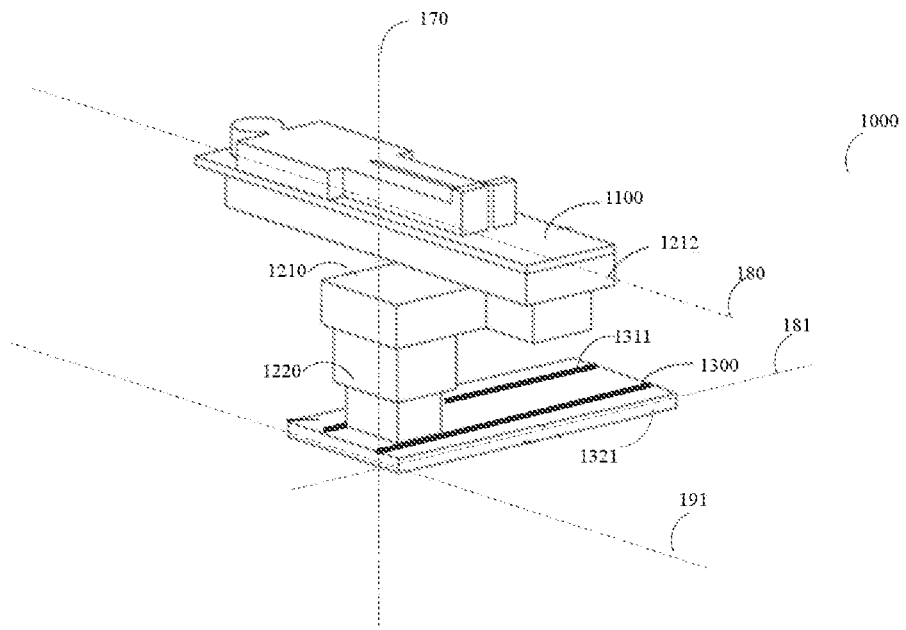

FIG. 2 shows an exemplary supporting system according to some embodiments. As shown in FIG. 2, in some embodiments, the support device 1200 described in FIG. 1 may further include a second holder 1212. The second holder 1212 may be located between the table 1100 and the first holder 1210. The first holder 1210 may be fixedly or slidably connected to the second holder 1212. The second holder 1212 may be fixedly to or slidably connected to the table 1100. In some embodiments, at least a portion of the second holder 1212 may protrude outside of the support device 1200. In some embodiments, at least a portion of the second holder 1210 may extend along the width direction of the table 1100. In some embodiments, the projection of the region (or referred to as contact area) of the second holder 1212 that contacts, supports, or is connected to the table 1100 may partially overlap with the projection of the region (or referred to as contact area) of the first holder 1210 that contacts, or is supported by or connected to the sliding device 1220; one or both of the projections may be onto the ground or the plane where a guide device 1300 (described elsewhere in the present disclosure) is located. As used herein, a projection of a region may refer to the reproduction of an object upon a plane or a curved surface by projecting the points on the object. As used herein, that a first projection overlaps with a second projection may indicate that the first projection falls within the second projection, and no area of the first projection falls outside of the second projection, or vice versa. As used herein, that a first projection partially overlaps with a second projection may indicate that at least some area of the first projection falls outside of the second projection. As used herein, that a first projection does not overlap with a second projection may indicate that the first projection falls outside of the second projection. In some embodiments, the projection of the region (or referred to as contact area) of the second holder 1212 that contacts, supports, or is connected to the table 1100 does not overlap with the projection of the region (or referred to as contact area) of the first holder 1210 that contacts, or is supported by or connected to the sliding device 1220; one or both of the projections may be onto the ground or the plane where a guide device 1300 (described elsewhere in the present disclosure) is located. In some embodiments, the second holder 1212 may be configured to rotate around the driving device placed between the first holder 1210 and the second holder 1212, causing the table 1100 to rotate.

In some embodiments, the driving device (not shown in FIG. 1 or FIG. 2) may be configured to drive the support device 1200 to move relatively to the guide device 1300. In some embodiments, the driving device may be configured to drive the support device 1200 to move relatively to the guide device 1300 along the length direction 181 of the guide device 1300. In some embodiments, the driving device may be configured to drive the support device 1200 to move relatively to the guide device 1300 along the width direction 191 of the guide device 1300.

In some embodiments, the driving device may be configured to drive the table 1100 to move relatively to the support device 1200. In some embodiments, the driving device may be configured to drive the table 1100 to move relatively to the support device 1200 along the length direction 180 of the table 1100. In some embodiments, the driving device may be configured to drive the table 1100 to move relatively to the support device 1200 along the width direction 190 of the table 1100. In some embodiments, the driving device may be configured to drive the table 1100 to rotate relatively to the support device 1200 around a shaft placed between the table 1100 and the support device 1200.

In some embodiments, the driving device may be configured to drive the second holder 1212 to rotate relatively to the first holder 1210 around a shaft placed between the second holder 1212 and the first holder 1210. In some embodiments, the driving device may be configured to drive the support device 1200 to rotate relatively to the guide device 1300 around a shaft placed between the support device 1200 and the guide device 1300. It should be appreciated by those skilled in the art that number and function of the driving device are not limited to the embodiments mentioned hereinabove.

The length direction 180 of the table 1100 and the length direction 181 of the guide device 1300 may be parallel to each other, as shown in FIG. 1, or form a particular angle ranging from 0 degree to 90 degrees. In some embodiments, the particular angle between the length direction 180 of the table 1100 and the length direction 181 of the guide device 1300 may be approximately 90 degrees, as shown in FIG. 2. The width direction 190 of the table 1100 and the width direction 191 of the guide device 1300 may be parallel to each other, as shown in FIG. 1, or form a particular angle ranging from 0 degree to 90 degrees. In some embodiments, the particular angle between the length direction 180 of the table 1100 and the length direction 181 of the guide device 1300 may be approximately 90 degrees, as shown in FIG. 2.

FIG. 3 through FIG. 6 show exemplary driving devices in accordance with some embodiments of the present disclosure.

Figure 3:
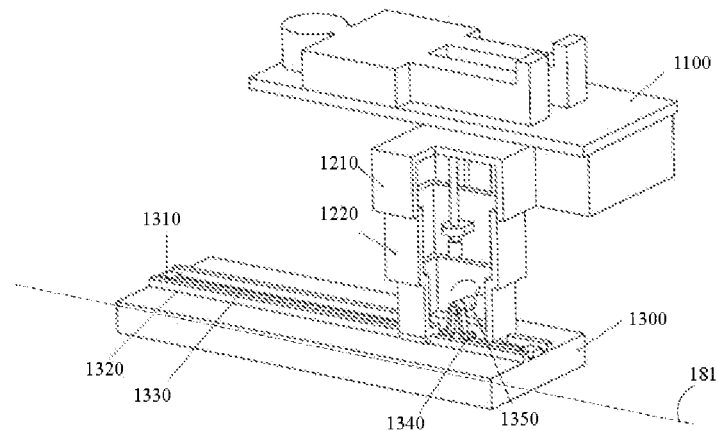
FIG. 3 and FIG. 4 are perspective views of different driving devices according to some embodiments of the present disclosure.

As shown in FIG. 3, a driving device 13 for driving the support device 1200 to move on the guide device 1300 may include a belt 1330, a motor 1350, a pinch roller 1340, and a belt block 1310.

For illustration purposes, the guide rail 1320 may be placed on the guide device 1300 along the length direction 181 of the guide device 1300. The support device 1200 may be slidably connected to the guide rail 1320 and the belt 1330. The motor 1350 may be fixed on the support device 1200. The belt block 1310 may be configured to stable the belt 1330 in the slot between the guide rails 1320. The pinch roller 1340 may be configured to press the belt 1330 on motor output shaft of the motor 1350. When the motor starts to work, the motor output shaft may drive the belt 1330, and the belt 1330 may drive the support device 1200 to move along the length direction 181 of the guide device 1300. It should be appreciated by those skilled in the art that other driving devices may also be used to drive the support device 1200 moving on the guide device 1300, and the driving device disclosed herein may be used for controlling other component relative movements described in present disclosure.

It should be noted that the above descriptions are for illustration purposes and not intended to limit the scope of the present disclosure. For persons having ordinary skills in the art, multiple variations and modifications may be made under the teachings of the present disclosure. However, those variations and modifications do not depart from the scope of the present disclosure. For example, position of the driving device 13 may be various. Position and number of the belt 1330, the motor 1350, the pinch roller 1340 and the belt block 1310 may be various. Length and width of the belt 1330 may be various. The shape of the guide rail 1320 may be various. Merely by way of example, the shape of the guide rail 1320 may be U-shape or S-shape.

Figure 4:
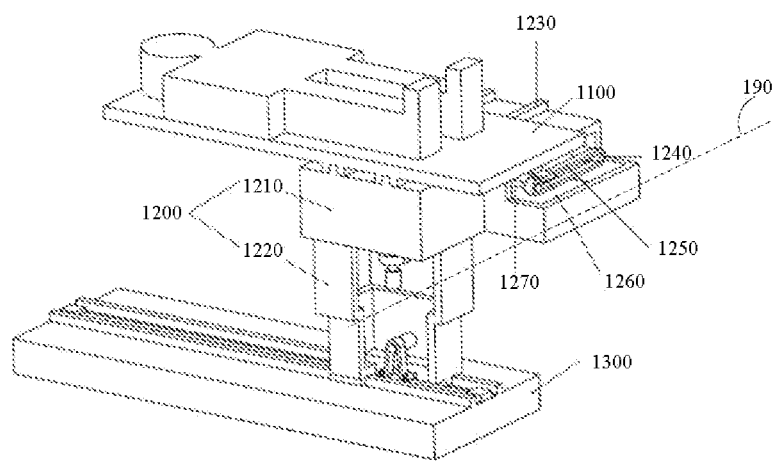

FIG. 4 shows another embodiment of a driving device. As shown in FIG. 4, a driving device 12 for driving the table 1100 to move on the support device 1200 may include a guide rail 1230, a belt 1250, a belt shaft 1270, a motor 1240, and a slider 1260.

For illustration purposes, the guide rail 1230 may be placed on the support device 1200 along the width direction 190 of the table 1100. The table 1100 may be fixedly connected to the slider 1260. The belt 1250 may be set on the belt shaft 1270 and the motor output shaft of the motor 1240. When the motor 1240 starts to work, the motor output shaft may drive the belt 1250, the belt 1250 may drive the slider 1260, and the slider 1260 may drive the table 1100 to move along the width direction 190 of the support device 1200. It should be appreciated by those skilled in the art that other driving devices may also be used to drive the table 1100 moving on the support device 1200, and the driving device disclosed herein may be used for controlling other component relative movements described in present disclosure.

It should be noted that the above descriptions are for illustration purposes and not intended to limit the scope of the present disclosure. For persons having ordinary skills in the art, multiple variations and modifications may be made under the teachings of the present disclosure. However, those variations and modifications do not depart from the scope of the present disclosure. For example, the position of the driving device 12 may be various. The position and the number of the guide rail 1230, belt 1250, belt shaft 1270, motor 1240, slider 1260 may be various. The length and the width of the belt 1250 may be various. Merely by way of example, the shape of the guide rail 1230 may be U-shape or S-shape.

Figure 5:
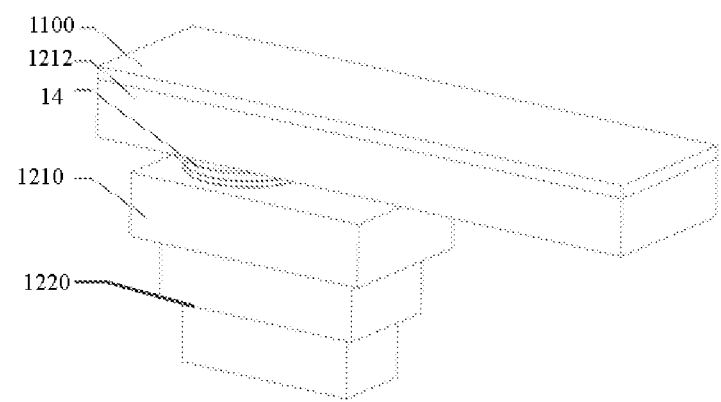
FIG. 5 and FIG. 6 show exemplary driving devices for rotation in a supporting system according to some embodiments of the present disclosure.
Figure 6:
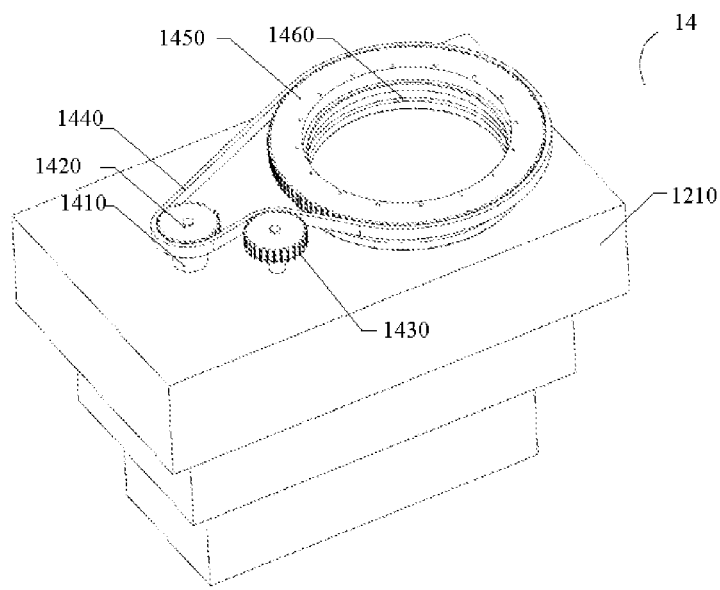

FIG. 5 and FIG. 6 show exemplary driving devices for rotation in accordance with some embodiments of the present disclosure. As shown in FIG. 5, driving device 14 may exist between the first holder 1210 and the second holder 1212. The driving device 14 may be configured to drive the second holder 1212 rotating around the driving device 14, and the table 1100 may be driven to rotate around the driving device 14.

As shown in FIG. 6, the driving device 14 may include a motor 1410, a first wheel 1420, a second wheel 1430, a belt 1440, a third wheel 1450, and a driving bearing 1460.

For illustration purposes, one end of the motor 1410 may be fixed to the first holder 1210. The motor output shaft of the motor 1410 may be fixed to the first wheel 1420. The rotation of the first wheel 1420 may drive the belt 1440. The first wheel 1420 may be configured to drive the belt 1440. The second wheel 1430 may be configured to press the belt 1440 to avoid the malposition thereof. One side of the third wheel 1450 may be fixed to the second holder 1212. The other side of the third wheel 1450 may be rotatably connected to the driving bearing 1460. The driving bearing 1460 may be configured to support the third wheel 1450. The driving bearing 1460 may be fixed to the first holder 1210. The movement of the belt 1440 may drive the third wheel 1450 to rotate. When the motor start to work, the first wheel 1420 may rotate and drive the belt 1440, the belt 1440 may drive third wheel 1450 to rotate, and the third wheel 1450 may drive the second holder 1212 to rotate around the driving bearing 1460.

It should be noted that the above descriptions are for illustration purposes and not intended to limit the scope of the present disclosure. For persons having ordinary skills in the art, multiple variations and modifications may be made under the teachings of the present disclosure. However, those variations and modifications do not depart from the scope of the present disclosure. For example, the position of the driving device 14 may be different than that shown in FIG. 5, the driving device 14 may exist randomly between the first holder 1210 and the second holder 1212. The placement of the driving device 14 may be different than that illustrated in FIG. 5, in which the driving device 14 may be placed between the first holder 1210 and the second holder 1212. The driving device 14 may be placed between the second holder 1212 and the table 1100. The position and the number of the motor 1410, the first wheel 1420, the second wheel 1430, the belt 1440, the third wheel 1450 and the driving bearing 1460 may be various. The shape of the third driving motor 1410, the first wheel 1420, the second wheel 1430, the third wheel 1450, and/or the driving bearing 1460 may be circular or essentially circular. The diameter and the height of the third driving motor 1410, the first wheel 1420, the second wheel 1430, the third wheel 1450, and the driving bearing 1460 may be various. The length and the width of the belt 1440 may be various. The shaping of the first wheel 1420, the second wheel 1430, the third driving belt 1440, the third wheel 1450 and the bearing 1460 may be various. Merely by way of example, the shaping of the first wheel 1420, the belt 1440, and the third wheel 1450 may be a gear shape. Thus the belt 1440 and the second wheel 1430 may be omitted, the first wheel 1420 may drive the third wheel by directly gear meshing.

Figure 7:
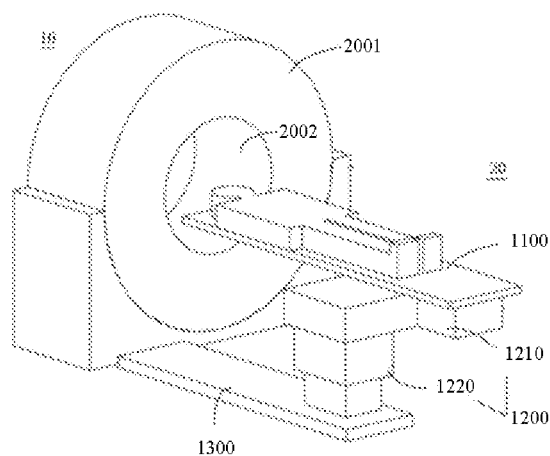
FIG. 7 to FIG. 12 illustrate exemplary supporting systems in various multi-modality diagnostic imaging systems according to some embodiments of the present disclosure.
Figure 8:
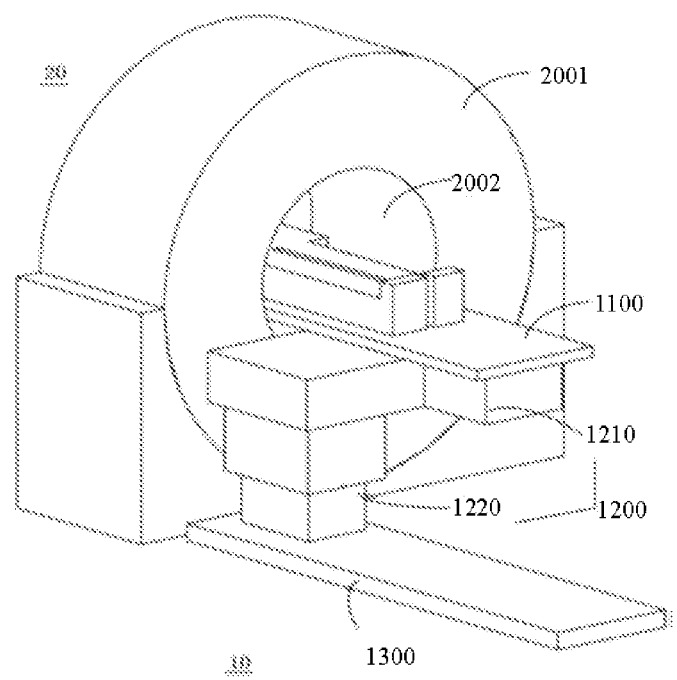
Figure 9:
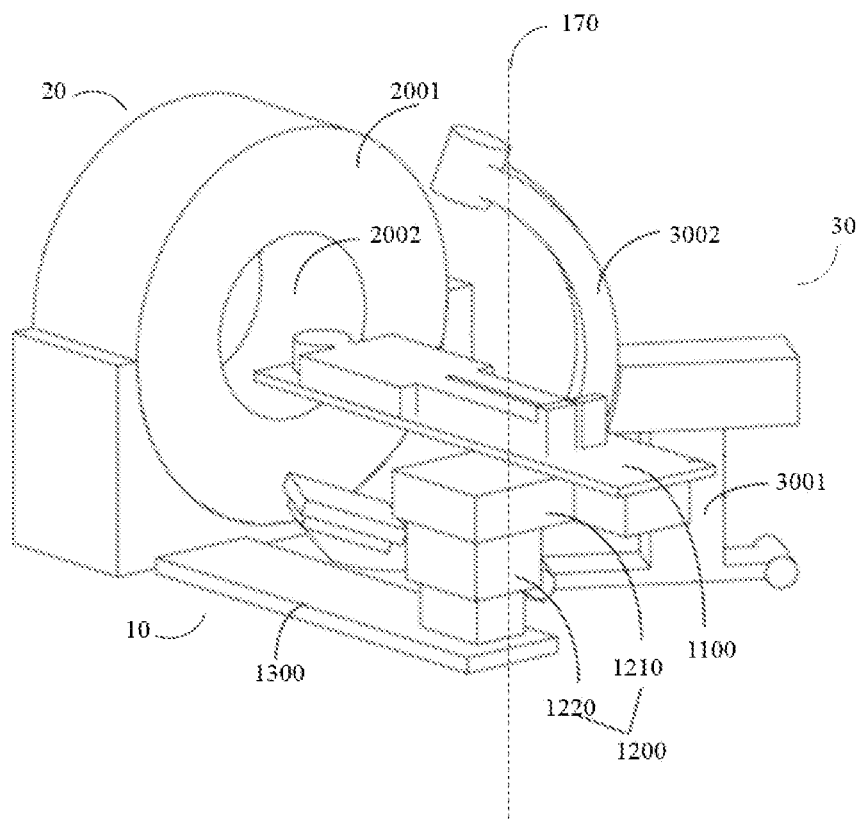

FIG. 7 to FIG. 12 illustrate exemplary multi-modality diagnostic imaging systems according to some embodiments of the present disclosure. As shown in FIG. 9, the multi-modality diagnostic imaging system may include a CT imaging system 20, an angiography system 30, and a supporting system 10. It should be appreciated by those skilled in the art that the diagnostic imaging method is not limited to CT and angiography. Exemplary diagnostic imaging methods or examination devices may include a magnetic resonance imaging (MM) system, an ultrasound scanning (US) system, a positron emission tomography (PET) system, a single-photon emission computerized tomography (SPECT) system, a CT-MR system, a CT-PET system, a CE-SPECT system, a DSA-MR system, a PET-MR system, a PET-US system, a SPECT-US system, a TMS (transcranial magnetic stimulation)-MR system, an US-CT system, an US-MR system, an X-ray-CT system, an X-ray-MR system, an X-ray-portal system, an X-ray-US system, a Video-CT system, a Vide-US system, or the like, or any combination thereof.

CT imaging system 20 may include a gantry 2001, an imaging volume 2002, and imaging components placed in the gantry 2001 (not shown in the figure). Axis of the imaging volume 2002 may be parallel to the length direction of the table 1100. When CT scanning procedure is operated, the imaging components placed in the gantry 2001 may be used to take images of region of interest of a patient or an object.

Angiography system 30 may comprise seat 3001, C-shaped arm 3002 sliding connected to the seat 3001, emitter and detector separately attached on both ends of the C-shaped arm 3002. When the angiographer 30 operating angiography process, the C-shaped arm may surround the patient or the object and the patient or the object is placed in the middle of the emitter and the detector, while radial emitted by the emitter may go through the region of interest of the patient or the object and may be received by the detector. Then images of the region of interest of the patient or the object may be generated by the signal from the detector.

FIG. 7 to FIG. 9 illustrate exemplary multi-modality diagnostic imaging systems using the supporting system disclosed herein that the table is fixed connected to the first holder 1210 according to some embodiments of the present disclosure. As shown in FIG. 7 and FIG. 8, when a CT scanning procedure is operated, the patient or the object may lie on the table 1100. The sliding device 1220, driven by the driving device, may move along the guide device 1300 along the length direction 180 and approach the imaging volume 2002. Then the table 1100 may enter the imaging volume 2002, and images of the region of interest of the patient or the object may be generated. After the CT scanning procedure completes, the sliding device 1220, driven by the driving device 13 (not shown in the figure), may move along the guide device 1300 along the length direction 180 of the table 1100, and depart the imaging volume 2002, causing the table 1100 to exit the imaging volume 2002.

After the CT scanning procedure completes, the patient or the object may further need angiography. As shown in FIG. 9, at least a portion of the first holder 1210 may protrude outside of the support device 1200. At least a portion of the table 1100 may not overlap with the guide device 1300. In some embodiment, at least a portion of the first holder 1210 may extend along the width direction of the table 1100. In some embodiments, the projection of the region (or referred to as contact area) of the first holder 1210 that contacts, supports, or is connected to the table 1100 may partially overlap with the projection of the region (or referred to as contact area) of the first holder 1210 that contacts, or is supported by or connected to the sliding device 1220; one or both of the projections may be onto the ground or the plane where the guide device 1300 (described elsewhere in the present disclosure) is located. In some embodiments, the projection of the region (or referred to as contact area) of the first holder 1210 that contacts, supports, or is connected to the table 1100 does not overlap with the projection of the region (or referred to as contact area) of the first holder 1210 that contacts, or is supported by or connected to the sliding device 1220; one or both of the projections may be onto the ground or the plane where the guide device 1300 (described elsewhere in the present disclosure) is located. A space formed by the guide device 1300, the sliding device 1220, and the first holder 1210 may be used to accommodate the angiography device 30. When sequentially operating CT scanning and angiography, the patient or the object do not need to move from one table to the other one. The position of the patient or the object relative to the table may remain essentially the same between examinations. The position of the patient or the object on the table 1100 does not need to be adjusted for in a different examination system. In some embodiments, the sliding device 1220 may include an extendable structure that may extend or contract in the vertical direction 170, causing the table 1100 to move in the vertical direction such that the distance between the plane of the table 1100 and the guide device 1300 may be adjusted.

Figure 10:
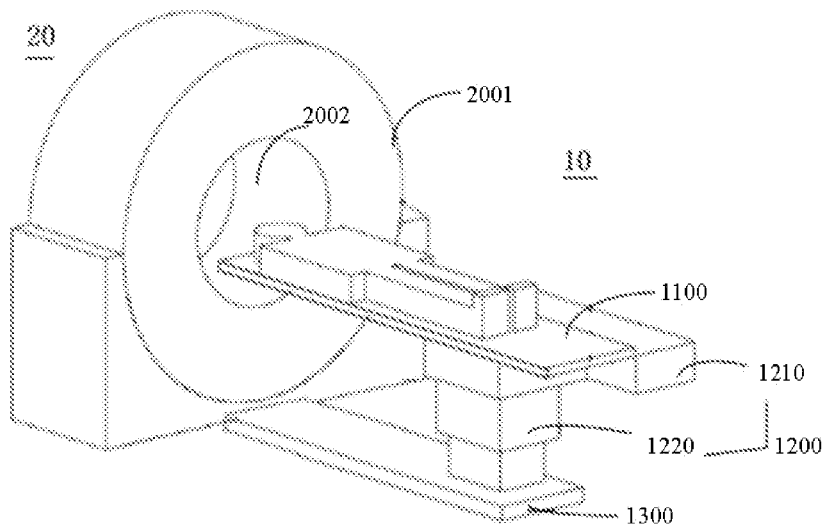
Figure 11:
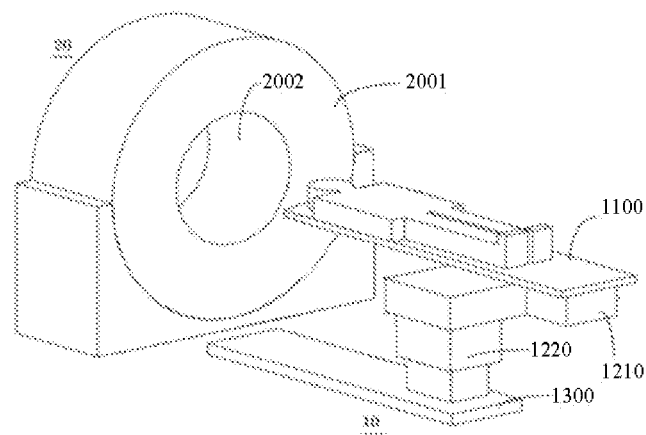

FIG. 10 to FIG. 11 illustrate exemplary supporting systems in multi-modality diagnostic imaging systems according to some embodiments of the present disclosure. The table 1100 may be slidably connected to the first holder 1210 according to some embodiments of the present disclosure.

When a CT scanning is performed, as shown in FIG. 10, the center line of the guide device 1300 along the length direction of the table 1100 may align with the axis of the gantry in a same vertical plane. The sliding device 1220 moving along the length direction of the guide device 1300 and convey the table 1100 into the gantry for generating CT images of the region of interest of the patient or the object.

After the CT scanning procedure completes, as shown in FIG. 11, the sliding device 1220 may move long the guide device 1300 and retract the table 1100 away from the gantry. Then the table 1100 may move along the width direction of the table 1100 and away from the sliding device 1220. The first holder 1210 may extend along the width direction of the table 1100. Thus when the table 1100 moves to the extension area, the projection of the region (or referred to as contact area) of the first holder 1210 that contacts, supports, or is connected to the table 1100 does not overlap with the projection of the region (or referred to as contact area) of the first holder 1210 that contacts, or is supported by or connected to the sliding device 1220; one or both of the projections may be onto the ground or the plane where the guide device 1300 (described elsewhere in the present disclosure) is located. Meanwhile, the table 1100 does not overlap with the guide device 1300. A space formed by the guide device 1300, the sliding device 1220, and the first holder 1210 may accommodate the angiography device 30. When the angiographer 30 operating angiography procedure, the C-shaped arm may occupy the space and be positioned close to the patient or the object for examination. The patient or the object may be placed between the emitter and the detector, while radiation emitted by the emitter may pass through the region of interest of the patient or the object and may be received by the detector.

Figure 12:
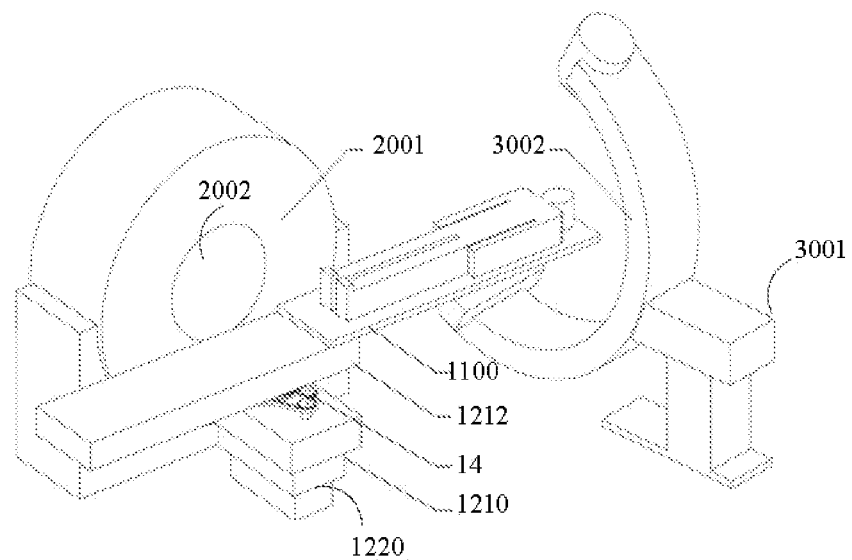

FIG. 12 illustrates an exemplary multi-modality diagnostic imaging system according to some embodiments of the present disclosure. As shown in FIG. 12, when CT scanning procedure is operated, the patient or the object may lie on the table 1100. The table 1100 may enter the imaging volume 2002 by changing position of the table 1100. The table 1100, driven by the driving device, may move along the second holder 1212. The table 1100, driven by the driving device 14, may rotate around the second holder 1212. Height of the table 1100 relative to the ground may be controllable by adjusting height of the sliding device 1220. Then the table 1100 may enter the imaging volume 2002, thus the imaging components placed in the gantry 2001 may generate images of the region of interest of the patient or the object.

After the CT scanning procedure completes, the table 1100, driven by the driving device, may be configured to move along the second holder 1212 and depart the imaging volume 2002, thus the table 1100 depart the imaging volume 2002. Then the table 1100, driven by the driving device 14, may rotate around the second holder and may align the center line of the table 1100 along the length direction in a same vertical plane with axis of C-arm of the angiographer. Then, the table 1100 may be configured to further move along the second holder 1212 to reach predetermined position relative to the C-arm.

FIGS. 13*a*, 13*b*, 14 and 15 illustrate a head supporting device to help the patient to easily and quickly adjust to a desired head posture and to maintain the posture during the examination.

Examples of such examinations that the head supporting device may be used in may include but not limit to a digital subtraction angiography (DSA) system, a Magnetic Resonance Imaging (MRI) system, a magnetic resonance angiography (MRA) system, a computed tomography (CT) system, a computed tomography angiography (CTA) system, an ultrasound scanning (US) system, a positron emission tomography (PET) system, a single-photon emission computerized tomography (SPECT) system, a CT-MR system, a CT-PET system, a CE-SPECT system, a DSA-MR system, a PET-MR system, a PET-US system, a SPECT-US system, a TMS (transcranial magnetic stimulation)-MR system, an US-CT system, an US-MR system, an X-ray-CT system, an X-ray-MR system, an X-ray-portal system, an X-ray-US system, a Video-CT system, a Vide-US system, or the like, or a combination thereof.

In some embodiments, the angles and the structure of the head supporting device may be designed so that once the patient places the head on the head supporting device, the head of the patient may be positioned to a desirable position in an examination of, for example, the head. In some embodiments, the head supporting device may include multiple surfaces with different angles and/or surface contours. In some embodiments, the head supporting device may be detachably assembled using a plurality of parts.

Figure 13A:
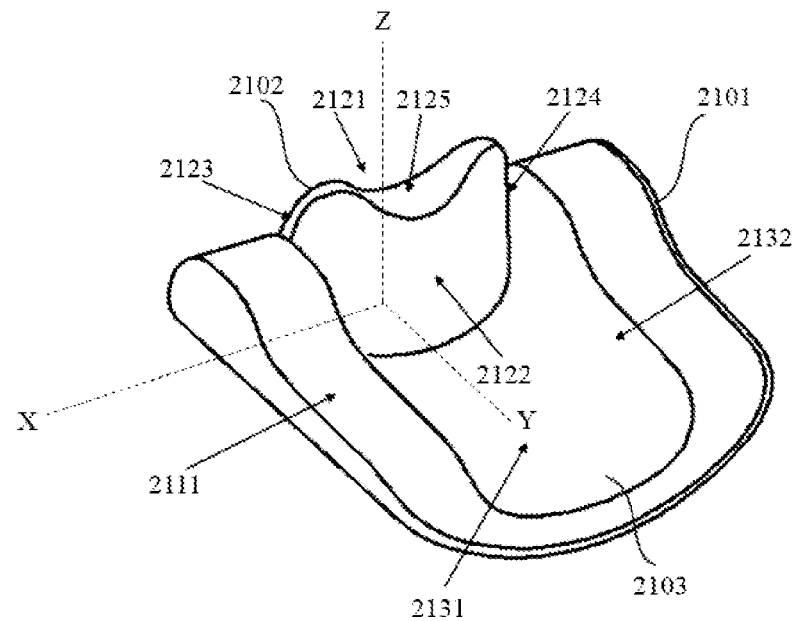
FIG. 13a and FIG. 13b illustrate exemplary configurations of a head supporting device according to some embodiments of the present disclosure.
Figure 13B:
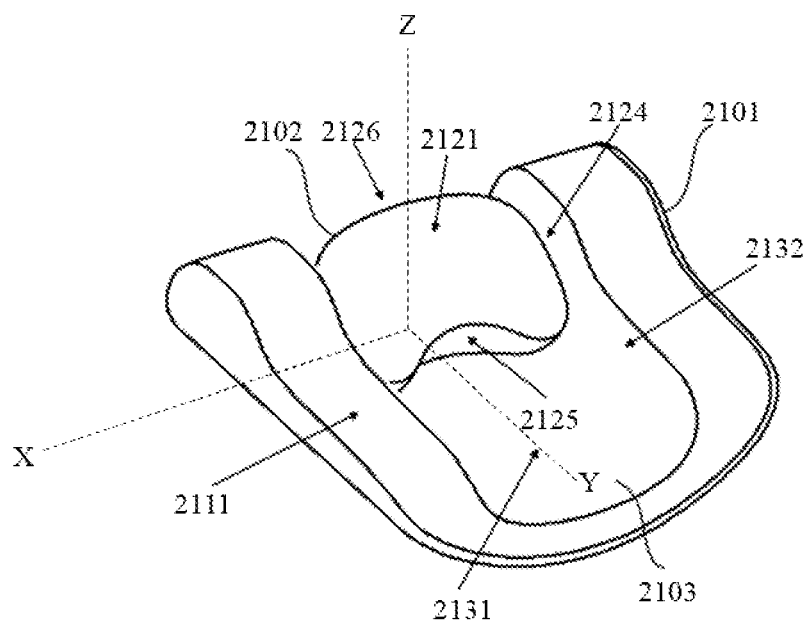

In some embodiments, the angles and the surface contours of the surfaces of the head supporting device may be configured so that when the patient lays his head on the head supporting device, a particular angle may be maintained between the geometric reference such as the vertical direction Z (as shown in FIG. 13*a* and FIG. 13*b*) or the horizontal direction (that may be perpendicular to the vertical direction) and a referenced line or plane in body of the patient. In some embodiments, the angle may be configured and maintained in the examination to obtain a clearer image. In some embodiments, the angle may be configured and maintained in the examination to immobilize the patient for generating a more stable image. In some embodiments, the angle may be configured and maintained in the examination to reduce the artifacts wherein the artifacts may be caused by a scan in a section where human tissues overlap or by an unexpected movement of the human body. In some embodiments, the angle configured and maintained in the examination may relate to the comfortableness of patient or any other issues.

In some embodiments, the angles and the structures of the head supporting device may be configured so that when the patient lays his head on the head supporting device, the angle between the vertical direction Z (as shown in FIG. 13*a* and FIG. 13*b*) and a reference line within the head of the patient such as an orbitomeatal line (hereinafter referred to as OML) or a canthomeatal line may be a constant. In some embodiments, the angle between the vertical and the OML may be a constant value as needed in a particular type of examination. In some embodiments, the angle between the vertical and the OML may be between 15 and 20 degrees. The head supporting device may be used in a radiation therapy such as X-ray, CT scan, MRI, etc.

FIG. 13*a* and FIG. 13*b* illustrate two configurations of a head supporting device used for a CT scan of the coronal section of a patient. As shown in FIG. 13*a* and FIG. 13*b*, the head supporting device may include a frame 2101 and a pad 2102. The frame 2101 may support the shoulders of the patient. The pad 2102 may support the head of the patient. The pad 2102 of the head supporting device may have a first configuration as illustrated in FIG. 13*a*, and a second configuration as illustrated in FIG. 13*b*. The frame 2101 may include a groove 2103 with a particular shape. The groove 2103 may be essentially flat (also referred to as the XY plane) on the frame 2101.

In some embodiments, the length of the pad 2102 may match at least the width or the length of the groove 2103 of the frame 2101 so that the frame 2101 and the pad 2102 may be connected. In some embodiments, the groove 2103 may be rectangular wherein its length is greater than the width, and the pad 2102 may be configured to match the width of the groove 2103 so that the pad 2102 may be connected or folded into the groove 2103. In some embodiments, the groove 2103 may be oval or circular, and the pad 2102 may be configured to match the length of the diameter (major axis if oval) of the groove 2103 so that the pad 2102 may be connected or folded into to the groove 2103.

In some embodiments, the pad 2102 may be fastened to the groove 2103 of the frame 2101 by a roller (not shown in the figure) through the pad 2102 in the width direction, as illustrated in FIG. 13*a* and FIG. 13*b*. In some embodiments, the surface of the pad 2102 and frame 2101 may be made of a friction material so that when the pad 2102 is folded into the groove 2103 of the frame 2101, the frictional force between them may be high enough to immobilize the pad 2102. In some embodiments, the pad 2102 may be of an elastic material including, for example, rubber, or the like. The pad 2102 may be compressed, folded into the groove 2103 and then expand within it, so that the pad 2102 may be immobilized or confined in the groove 2103. In some embodiments, the groove 2103 may be made of a first material and the pad 2102 may be made of a second material, wherein the first material and the second material may be sticking or attractive to each other. In some embodiments, the first material and the second material may be Velcro™ or magnetic materials, respectively.

The pad 2102, as shown in FIG. 13*a* and FIG. 13*b*, may include a first surface 2125, an undersurface 2126, a first side 2121, and a second side 2122. The first side 2121 may meet the first surface 2125 and the undersurface 2126. The second side 2122 may meet the first surface 2125 and the undersurface 2126. In some embodiments, the first side 2121 and the second side 2122 may be opposite to each other.

FIG. 13*a* illustrates an exemplary head supporting device. The head supporting device may be used in, for example, a CT scan when the patient is prone. More specifically, the undersurface 2126 of pad 2102 may be connected to the groove 2103 so that the jaw of the patient may be supported by the first surface 2125 of the pad 2102. In some embodiments, the undersurface 2126 may directly contact the bottom surface 2131 of the groove 2103.

FIG. 13b illustrates an exemplary head supporting device. The head supporting device may be used in, for example, a CT scan when the patient is supine. More specifically, the second side 2122 of the pad 2102 may be connected to the groove 2103 so that the patient's neck may be supported by the first side 2121 of the pad 2102 and the head of the patient may be supported by the undersurface 2126 of the pad 2102. In some embodiments, the second side 2122 of the pad 2102 may directly contact the bottom surface 2131 of the groove 2103. In some embodiments, the first side 2121 and the undersurface 2126 may be configured into a continuous and unitary surface to concurrently support patient's head and neck when the patient is supine (lying on the back).

In some embodiments, the angle between the second side 2122 and the undersurface 2126 may be chosen such that a desirable angle between the vertical direction and the OML of a patient may be achieved. For instance, if the desirable angle is between 15 degrees and 20 degrees, the angle between the second side 2122 and the undersurface 2126 may be between 70 and 75 degrees. To be illustrative, an intersection line may be formed by a plane perpendicular to a length direction of the groove 2103 intersecting the undersurface 2126 and another intersection line may be formed by a plane perpendicular to the length direction of the groove 2103 intersecting the second side 2122, wherein the angle between two intersection lines may be between 70 degrees and to 75 degrees.

The head supporting device may be designed such that a desirable position when a patient lays his head on the head supporting device may be achieved. In some embodiments, the desired position may be indicated by a desired angle between the vertical direction and a reference line within the head of the patient such as an OML or a canthomeatal line. Merely by way of example, if the desirable angle is A or between A and B, the angle between the second side 2122 and the undersurface 2126 may be (90–A) degrees or between (90–A) degrees and (90–B) degrees. An intersection line may be formed by a plane perpendicular to a length direction of the groove 2103 intersecting the undersurface 2126 and another intersection line may be formed by a plane perpendicular to the length direction of the groove 2103 intersecting the second side 2122, wherein the angle between two intersection lines may be (90–A) degrees or between (90–A) degrees and (90–B) degrees.

In some embodiments, when the patient is prone (lying on the stomach) and supports his jaw on the first surface as described elsewhere in the present disclosure, the OML may form an angle between 15 and 20 degrees with the vertical direction. In some embodiments, the patient may be supine and may support his head and neck on the continuous surface formed by the first side and the undersurface as described elsewhere in the present disclosure. In this case, as the angle between the second side 2122 and the undersurface of pad 2102 is between 70 and 75 degrees, the OML may also form an angle between 15 and 20 degrees with the vertical.

Refer again to FIG. 13a and FIG. 13b, the frame 2101 may also include two step surfaces 2111 in a length direction of the groove 2103. Each step surface 2111 may be located on one side of the groove 2103. In some embodiments, the step surfaces 2111 may be a continuous surface including at least a lower surface and a higher surface. The lower surface and the higher surface may be connected by a curved transition surface. Accordingly, when a patient lays his head pronely or supinely on the head supporting device, his shoulders may lie on the lower surface and contact the transition surface so that the patient may be positioned as needed in an examination.

Figure 14:
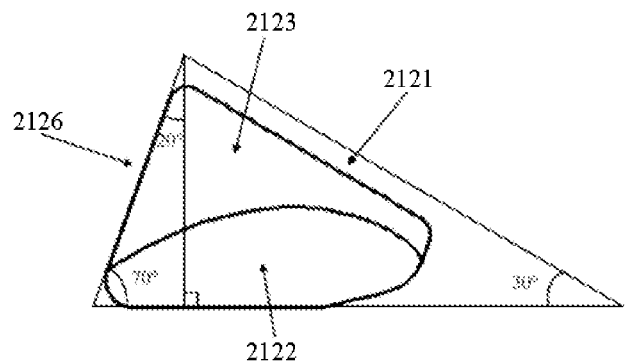
FIG. 14 illustrates an exemplary pad structure of a head supporting device according to some embodiments of the present disclosure.

FIG. 14 illustrates a side view of the pad 2102 of the head supporting device. The first side 2121, the second side 2122 and the undersurface 2126 may form a triangle (or quasi-triangle) in the side view. As shown in FIG. 14, the angle between the first side 2121 and the second side 2122 may be between 20 and 60 degrees. To be illustrative, an intersection line may be formed by a plane perpendicular to a length direction of the groove 2103 intersecting the first side 2121 and another intersection line may be formed by a plane perpendicular to the length direction of the groove 2103 intersecting the second side 2122, wherein the angle between two intersection lines may be between 20 and 60 degrees. Accordingly, the center of gravity of the pad 2102 may be within the triangle formed by first side 2121, the second side 2122 and the undersurface 2126, during both prone scan and supine scan so that the pad 2102 may provide sufficient support for patient during both scans.

In some embodiments, the angle between the first side 2121 and the second side 2122 may be configured to be 30 degrees and the angle between the second side 2122 and the undersurface 2126 may be configured to be 70 degrees, so that the undersurface 2126 may form an angle of 20 degrees with the plane perpendicular to the base of the triangular shape as shown in FIG. 14. Therefore, the OML may form a fixed angle of 20 degrees with the vertical.

Figure 15:
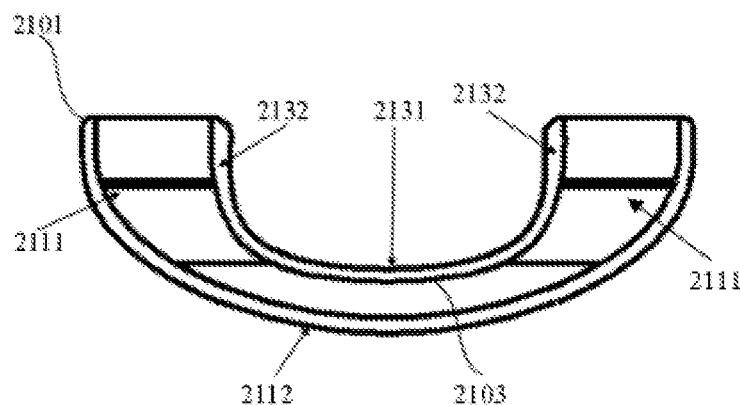
FIG. 15 illustrates an exemplary frame of a head supporting device according to some embodiments of the present disclosure.

FIG. 15 illustrates a front view of the frame 2101 of the head supporting device described in FIG. 13a and FIG. 13b. As shown in FIG. 15, the frame 2101 may include an outer bottom surface 2112. The outer bottom surface 2112 may have a particular shape and a bed or a table (not shown in the figure) which supports the patient in examination may be configured to match the shape of the outer bottom surface 2112 so that the bed may be connected to the outer bottom surface 2112. Refer to FIG. 13a and FIG. 15, the length direction of the groove 2103 of the frame 2101 may be consistent with the length direction of the bed. In some embodiments, the bottom surface 2112 may be arc-shaped, while the bed may have an arc-shaped groove to match at least the length or the width of the frame 2101. In some embodiments, the bed may be designed to include a plurality of grooves with different shapes so that different head supporting devices may be implanted and used in examination.

In some embodiments, the groove of the bed may be designed that the outer bottom surface 2112 of the frame 2101 may be able to move in the length direction of the bed. In some embodiments, an electric motor may be used to drive the frame 2101 of the head supporting device in the length direction of the bed so that the patient may be positioned as needed in the examination.

In some embodiments, refer to FIG. 13a and FIG. 15, the pad 2102 may include a third side 2123 and a fourth side 2124. The third side 2123 may meet the first surface 2125 and the undersurface 2126. The fourth side 2124 may meet the first surface 2125 and the undersurface 2126. In some embodiments, the third side 2123 and the fourth side 2124 may be opposite to each other. In some embodiments, the third side 2123 and the fourth side 2124 may be arranged in a direction perpendicular to the length direction of the groove 2103 in the horizontal plane.

In some embodiments, two side surfaces 2132 with a particular shape may be arranged at each side of the groove 2103. In some embodiments, the side surfaces 2132 may each contact the third side 2123 and the fourth side 2124 respectively. The pad 2102 may be able to move in the length direction of the groove 2103.

In some embodiments, the undersurface 2126 and the second side 2122 of the pad 2102 may match the shape of the inner bottom surface 2131. The third side 2123 and the fourth side 2124 may match the shape of the side surfaces 2132. Accordingly, the pad 2102 may be able to move in the length direction of the groove 2103 in both supine and prone scan. In some embodiments, the inner bottom surface 2131 and the outer bottom surface 2112 may be arc-shaped.

In some embodiments, the head supporting device may be made of a shape-memory material, i.e. a material which may maintain its shape when formed and may return to its pre-formed shape under special treatment such as heating. More specifically, a head supporting device which is made of the shape-memory material may be configured to the shape and structure as needed in an examination and be reshaped to the shape and structure as needed in another examination.

In some embodiments, an electrical shape-memory system may be implanted into the head supporting device of the present disclosure. The electrical shape-memory system may include a memory and a shape recovery circuit. The memory may store different shapes and structures as needed in different examinations. The shape recovery circuit may be used to change the head supporting device to any stored shapes or structures when a specific examination is implemented. In some embodiments, a cloud-based server may be implanted to the electrical shape-memory system so that when a patient takes the scan, the settings of the structures and shapes of the head supporting device may be stored in the cloud-based server. The head supporting device may be configured according to these stored settings when the patient once again takes the scan.

In some embodiments, a pre-examination check may be implemented before the examination. The check may include a step of monitoring the size and shape of the head of the patient. In some embodiments, the check may include touching the surface of the patient's head by hands. In some embodiments, the check may include graphical method of monitoring the size and shape of the head, wherein the graphical method may include but not limit to the use of one or more video cameras, the use of light emitters and sensors, etc.

In some embodiments, the patient may be classified into a plurality of groups based on an overall or a part of his body figure. In some embodiments, the patient may be grouped by the size and shape of his head, and the structure of head supporting device may be designed to specifically suit one or more of the groups. When the patient from that or those groups lays his head on the head supporting device, he may be positioned as needed by the examination.

This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. It should be appreciated for those skilled in the art that the head supporting device described in FIG. 13a and FIG. 13b may be used in a plurality of examinations and the angles may be adjustable depending on the type of the examination and/or other factors.

As also described elsewhere in the disclosure, a head supporting device, which may be used to immobilize patient's head during the examination to help to maintain a required position, may include a curved bottom surface. And the shape of a bed or a table used in diagnosis may be match the shape of the bottom surface so that the bed or the table may be connected to the head supporting device. In some embodiments, the supporting system described in FIG. 1 may be embedded with the head supporting device described in FIG. 13a. More specially, the table of the supporting system may match the shape of the bottom surface of the head supporting device such that both the head supporting device and the supporting system may be connected together.

Figure 16:
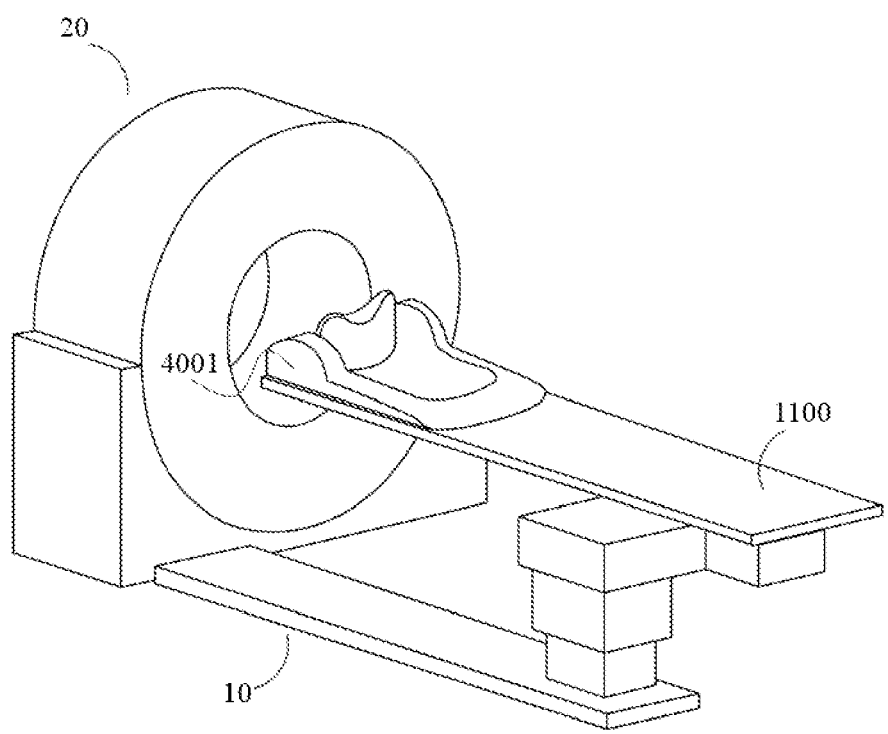
FIG. 16 illustrates a schematic diagram of a combined system according to some embodiments of the present disclosure.

FIG. 16 illustrates a schematic diagram of a combined system. The combined system may include a head supporting device with the supporting system. As shown in FIG. 16, the head supporting device 4001 may be placed on and/or connected to the table 1100 of the supporting system 10 and the neck and the head of the patient may be supported by the head supporting device 4001. As the head supporting device 4001 may be used to adjust and maintain the patient's head to a position as needed in the examination and the supporting system 10 may be used to position and transfer the patient relative to a plurality of examinations, the combined system may be able to adjust the patient to a position as needed in a first examination; to position and/or transfer the patient to a location as needed in the first examination; to help the patient to maintain the position as needed in a first examination; to position and/or transfer the patient to a second examination and to adjust the patient to another position as needed in the second examination.

In some embodiments, the table of the supporting system may include a groove matching the shape of the bottom surface of the head supporting device so that the head supporting device may be able to move in the length direction of the table. In some embodiments, when the head supporting device is moveably configured in the groove of the table, an electric motor may be used to drive the head supporting device in the length direction of the table so that the patient with different figures may be configured to diagnosis position as needed in the examination.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A head supporting device comprising:
    a frame for supporting a shoulder of a patient, the frame having a groove; and
    a pad for supporting the head of the patient, wherein the pad is placed on the frame and configured to move in a length direction of the groove, the length direction of the groove is consistent with a length direction of a bed, and the bed is configured to support the patient in examination;
    the pad comprising a first surface and a second surface, the pad having a first working position and a second working position;
    in the first working position of the pad, the first surface being configured to support the jaw of the patient when the patient is prone; and
    in the second working position of the pad, the second surface being configured to support the head and the neck of the patient when the patient is supine.

2. The head supporting device of claim 1, wherein the head supporting device is configured to position the head of the patient such that an angle between the plane perpendicular to the orbitomeatal line of the patient and a vertical direction is between 15 degrees and 20 degrees.

3. The head supporting device of claim 1, wherein
    the pad is embedded in the groove;
    the second surface comprises a first side and an undersurface, the first side being connected to the undersurface and the first surface, wherein
    when the patient is supine, the first side is used for supporting the neck of the patient and the undersurface is used for supporting the head of the patient.

4. The head supporting device of claim 3, wherein
    the pad comprises a second side connected to the first surface and the undersurface, the second side being opposite to the first side;
    when the patient is prone, the undersurface contacts a bottom of the groove; and
    when the patient is supine, the second side contacts at least a portion of the groove.

5. The head supporting device of claim 4, a first angle between a first intersection line of a second plane and the undersurface and a second intersection line of the second plane and the second side being between 70 degrees and 75 degrees, the second plane being perpendicular to a length direction of the groove.

6. The head supporting device of claim 5, a second angle between a third intersection line of the second plane and the first side and the second intersection line being from 20 degrees to 60 degrees.

7. The head supporting device of claim 4, wherein
    the pad comprises a third side and fourth side connected to the first surface and the undersurface, the third side and the fourth side being arranged opposite to each other along a direction perpendicular to the length direction of the groove in the horizontal plane.

8. The head supporting device of claim 7, wherein
    the groove comprises two side surfaces arranged two opposing sides of the groove, respectively, each of the two side surfaces contacting the third side and the fourth side of the pad, respectively.

9. The head supporting device of claim 7, wherein
    the shape of the undersurface and the shape of the second side of the pad match the shape of an inner bottom surface of the groove, and the shape of the third side and the shape of the fourth side of the pad match the shape of the two side surfaces of the groove.

10. The head supporting device of claim 9, wherein the shape of the inner bottom surface of the groove is arc-shaped.

11. The head supporting device of claim 1, wherein the frame includes an outer bottom surface, the shape of the outer bottom surface of the frame matching the shape of a bed that is configured to support the patient in an examination.

12. The head supporting device of claim 11, wherein the shape of the outer bottom surface of the frame is arc-shaped, and
the bed has an arc-shaped groove to match at least the length or the width of the frame.

13. The head supporting device of claim 1, wherein the frame includes two support parts in a length direction of the groove, each of the two support parts being located on one side of the groove.

14. The head supporting device of claim 13, wherein each of the two support parts has a step surface.

15. A medical device, wherein the medical device comprises a bed and the head supporting device of claim 1,
the head supporting device includes an outer bottom surface, the outer bottom surface being arranged contacting with the bed, the head supporting device is configured to move on the bed along the length direction of the bed.

16. The medical device of claim 15, wherein the shape of the outer bottom surface of the head supporting device matches the shape of the bed.

17. The medical device of claim 15, wherein the bed includes a groove matching the outer bottom surface of the head supporting device, the head supporting device being movably configured in the groove of the table.

18. The medical device of claim 15, wherein the head supporting device is configured to position the head of the patient such that an angle between the plane perpendicular to the orbitomeatal line of the patient and a vertical direction is between 15 degrees and 20 degrees.

19. The medical device of claim 15, wherein
the pad is embedded in the groove;
the second surface comprises a first side and an undersurface, the first side being connected to the undersurface and the first surface, wherein
when the patient is supine, the first side is used for supporting the neck of the patient and the undersurface is used for supporting the head of the patient.

20. The head supporting device of claim 1, wherein
the pad is fastened to the groove by at least one of a roller, a friction force between the pad and the groove, or a stickness or an attraction between the pad and the groove.

* * * * *